United States Patent
Zhang et al.

(10) Patent No.: US 10,398,804 B2
(45) Date of Patent: Sep. 3, 2019

(54) PROGENITOR CELLS FROM URINE AND METHODS FOR USING THE SAME

(75) Inventors: Yuanyuan Zhang, Winston-Salem, NC (US); Anthony Atala, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 774 days.

(21) Appl. No.: 12/601,028

(22) PCT Filed: May 20, 2008

(86) PCT No.: PCT/US2008/006438
§ 371 (c)(1),
(2), (4) Date: Jan. 8, 2010

(87) PCT Pub. No.: WO2008/153685
PCT Pub. Date: Dec. 18, 2008

(65) Prior Publication Data
US 2010/0158977 A1 Jun. 24, 2010

Related U.S. Application Data

(60) Provisional application No. 60/939,427, filed on May 21, 2007, provisional application No. 60/943,215, filed on Jun. 11, 2007.

(51) Int. Cl.
*A61F 2/00* (2006.01)
*A01N 65/00* (2009.01)
(Continued)

(52) U.S. Cl.
CPC ....... *A61L 27/3882* (2013.01); *A61L 27/3804* (2013.01); *C12N 5/0685* (2013.01);
(Continued)

(58) Field of Classification Search
None
See application file for complete search history.

(56) References Cited

U.S. PATENT DOCUMENTS

| 4,153,512 A | 5/1979 | Messner et al. |
| 5,912,116 A | 6/1999 | Caldwell |

(Continued)

FOREIGN PATENT DOCUMENTS

| JP | 2005-261292 | 9/2005 |
| JP | 2007-202512 | 8/2007 |

(Continued)

OTHER PUBLICATIONS

Forostyak et al. "CNS Regenerative Medicine and Stem Cells" Opera Med Physiol 2016, vol. 2(1): 55-62.*

(Continued)

*Primary Examiner* — Renee Claytor
*Assistant Examiner* — Lauren K Van Buren
(74) *Attorney, Agent, or Firm* — Myers Bigel, P.A.

(57) ABSTRACT

Provided herein are urine progenitor cells and methods for producing a culture of urine progenitor cells from a urine sample. The cells may be selected based upon the use of a selective cell medium, based upon morphology, and/or by selecting cell-specific markers. Also provided is an isolated urine progenitor cell that is c-kit positive and can differentiate into urothelium, smooth muscle, endothelium or interstitial cells. Methods of use of urine progenitor cells are provided, wherein cell are seeded onto a tissue scaffold are provided. Methods of treating a subject in need thereof are also provided, including providing a bladder tissue substrate that includes differentiated UPCs and transplanting the substrate into the patient. Finally, kits are provided that include a container suitable for the transport of a urine sample; media; one or more antibiotics; a package for holding said (Continued)

container, media, and antibiotics; and optionally, instructions for use.

18 Claims, 9 Drawing Sheets

(51) Int. Cl.

| | |
|---|---|
| *C12N 5/00* | (2006.01) |
| *C12N 5/02* | (2006.01) |
| *A61L 27/38* | (2006.01) |
| *C12N 5/071* | (2010.01) |
| *A61K 35/12* | (2015.01) |

(52) U.S. Cl.
CPC ........... *A61K 35/12* (2013.01); *A61L 2430/22* (2013.01); *C12N 2500/40* (2013.01); *C12N 2501/01* (2013.01); *C12N 2501/11* (2013.01); *C12N 2501/39* (2013.01); *C12N 2501/395* (2013.01)

(56) References Cited

U.S. PATENT DOCUMENTS

| | | | |
|---|---|---|---|
| 6,008,008 A | 12/1999 | James et al. | |
| 6,171,344 B1 | 1/2001 | Atala | |
| 6,235,527 B1 | 5/2001 | Rao et al. | |
| 6,444,205 B2 | 9/2002 | Dinsmore et al. | |
| 6,548,299 B1 | 4/2003 | Pykett et al. | |
| 6,723,131 B2 * | 4/2004 | Muschler | A61F 2/4644 623/23.51 |
| 2002/0012953 A1 | 1/2002 | Jauho et al. | |
| 2004/0152190 A1 * | 8/2004 | Sumita | C12N 5/0663 435/369 |
| 2005/0106634 A1 * | 5/2005 | Pfrieger et al. | 435/7.2 |
| 2005/0265978 A1 | 12/2005 | Chancellor et al. | |
| 2006/0039593 A1 | 2/2006 | Sammak et al. | |
| 2006/0153816 A1 | 7/2006 | Brown et al. | |
| 2007/0202536 A1 * | 8/2007 | Yamanishi et al. | 435/7.1 |
| 2007/0254295 A1 * | 11/2007 | Harvey | C12Q 1/6886 435/6.18 |
| 2008/0213230 A1 | 9/2008 | Phillips et al. | |

FOREIGN PATENT DOCUMENTS

| | | | |
|---|---|---|---|
| JP | 2007-284383 | 11/2007 | |
| WO | WO 2004/010852 A2 | 2/2004 | |
| WO | WO2004084950 | * 10/2004 | |
| WO | WO-2004084950 A2 * | 10/2004 | ............. A61K 38/17 |
| WO | WO 2006/026730 A2 | 3/2005 | |
| WO | WO-2005021738 A1 * | 3/2005 | ........... C12N 5/0607 |
| WO | WO 2005/033268 A2 | 4/2005 | |
| WO | WO 2005-047529 A1 | 5/2005 | |
| WO | WO 2006/135103 A1 | 12/2006 | |

OTHER PUBLICATIONS

Oliver "Avian Thymic Accesory Cells" Journal of Immunology, vol. 132, No. 4, Apr. 1984, 1748-1754.*
Sagrinati et al. "Isolation and Characterization of Multipotent Progenitor Cells from Bowman's Capsule of Adult Human Kidneys" Journal of Americal Society of Nephrology 17: 2443-2456, 2006.*
Freshney, Culture of Animal Cells A Manual of Basic Technique, 5th Edition, John Willey & Sons, 2005, 241-250.*
Ono Y et al. "Isolation and culture of tubular epithelial cells from cells in urine samples of a canine model of ischemica/reperfusion, and their potenital use for the treatment of renal failure." Report for Health and Labor Sciences Research Grants from 2005 to 2006, Mar. 2006, pp. 31-33, Translation of relevant portions. Provided by Applicants.*
Sagrinati et al. "Isolation and Characterizaiton of Multipotent Progenitor Cells from Bowman's Capsule of Adult Human Kidneys" Journal of American Society of Nephrology 17: 2443-2456, 2006.*
Ono Y et al. "Isolation and culture of tubular epithelial cells from cells in urine samples of a canine model of Ischemica/reperfusion, and their potential use for the treatment of renal failure." Report for Health and Labor Sciences Research Grants from 2005 to 2006, Mar. 2006, pp. 31-33, Translation of relevant portions. Provided by Applicants.*
Sagrinati et al. "Isolation and Characterization of Multipotent Progenitor Cells from Bowman's Capsule of Adult Human Kidneys." Journal of American Society of Nephrology 17: 2443-2456, 2006.*
Freshney, Culture of Animal Cells A Manual of Basic Techniques, 5th Edition, John Willey & Sons, 2005 241-250.*
Ono Y et al. "Isolation and culture of tubular epithelial cells from cells in urine samples of a canine model of ischemica/reperfusion, and their potential use for the treatment of renal failure." Report for Health and Labor Sciences Research Grants from 2005 to 2006, Mar. 2006, pp. 31-33, Translation of relevant portions. Provided by Applicant.*
Sagrinati et al. "Isolation and Characterization of Multipotent Progenitor Cellls from Bowman's Capsule of Adult Human Kidneys" Journal of America Society of Nephrology 17: 2443-2456, 2006.*
Sagrinati et al. "Isolation and Characterization of Multipotent Progenitor Cells from Bowman's Capsule of Adult Human Kidneys" Journal of America Society of Nephrology 17: 2443-2456, 2006.*
Freshney, Culture of Animal Cells A Manual of Basic Techniques, 5th Edition, John Wiley & Sons, 2005, 241-250.*
Sagrinati et al. "Isolation and Characterization of Multipotent Progenitor Cellls from Bowman's Capsule of Adult Human Kidneys" Journal of America Society of Nephrology 17: 2443-2456, 2006 (Year: 2006).*
Freshney, Culture of Animal Cells A Manual of Basic Techniques, 5th Edition, John Wiley & Sons, 2005, 241-250. (Year: 2005).*
Ono Y et al. "Isolation and culture of tubular epithelial cells from cells in urine sample of a canine model of ischemica/reperrfusion, and their potential use for treatment of renal failure." Report for Health and Labor Sciences Research Grants from 2005 to 2006, Mar. 2006, pp. 31-33, Translation of relevant portions. Provided by Applicant.*
http://www.yourdictionary.com/glomerulus.*
International Search Report and Written Opinion, PCT/US08/06438, dated Sep. 29, 2011.
International Written Opinion and Search Report, PCT/US2008/006438, dated Dec. 3, 2008.
Sagrinati C et al. Isolation and characterization of multipotent progenitor cells from the Bowman's capsule of adult human kidneys. Journal of the American Society of Nephrology. 2006; 17: 2443-2456.
Kitamura S et al. Establishment and characterization of renal progenitor like cells from S3 segment of nephron in rat adult kidney. The FASEB Journal. Nov. 2005; 19: 1789-1797.
Becker et al. "Stem Cells for Regeneration of Urological Structures", European Urology, Elsevier BV, NL, vol. 51, No. 5, Mar. 23, 2007, pp. 1217-1228, XP005934664.
Extended European Search Report for European Application No. 08754571.1 dated Nov. 29, 2010; 10 pages.
Zhang et al. "A Novel Cell Source for Urologic Tissue Reconstruction", Journal of Urology; AUA Annual Meeting 2007; Anaheim, CA, USA; May 21, 2007; Lippincott Williams & Wilkins, Baltimore, MD, US, vol. 177 No. 4, Supplement p. 238, Apr. 2007, XP008129230.
Zhang Y et al. Urine derived cells are a potential source for urological tissue reconstruction. The Journal of Urology. Nov. 2008; 180: 2226-2233.
Bodin A et al. Tissue-engineered conduit using urine-derived stem cells seeded bacterial cellulose polymer in urinary reconstruction and diversion. Biomaterials. Dec. 2010; 31(34): 8889-8901.

(56) References Cited

OTHER PUBLICATIONS

Felix JS et al. Human epithelial cells cultured from urine: growth properties and keratin staining. In Vitro. Oct. 1980; 16(10): 866-874 Abstract only.
Fernandez-Conde M et al. Bone metaplasia of urothelial mucosa: an unusual biological phenomenon causing kidney stones. Bone. Mar. 1996; 18(3): 289-291.
Dörrenhaus A et al. Cultures of exfoliated epithelial cells from different locations of the human urinary tract and the renal tubular system. Arch Toxicol. 2000; 74: 618-626.
Zhang YY et al. Expansion and long-term culture of differentiated normal rate urothelial cells in vitro. In Vitro Cell Dev Biol. Jul./Aug. 2001; 37: 419-429.
Inoue CN et al. Reconstruction of tubular structures in three-dimensional collagen gel culture using proximal tubular epithelial cells voided in human urine. In Vitro Cell Dev Biol. Sep./Oct. Sep.-Oct. 2003; 39(8-9): 365-367.
Staack A et al. Molecular, cellular and developmental biology of urothelium as a basis of bladder regeneration. Differentiation. 2005; 73: 121-133.
Atala A et al. Tissue-engineered autologous bladders for patients needing cystoplasty. The Lancet. Apr. 15, 2006; 367: 1241-46.
Chung SY. Bladder tissue-engineering: a new practical solution? The Lancet. Apr. 15, 2006; 367: 1215-16.
International Search Report and Written Opinion, PCT/US09/63706, dated Jan. 11, 2010.
Felix JS et al. Human epithelial cells cultured from urine: growth properties and keratin staining. In Vitro. Oct. 1980; 16(10): 866-74 Abstract.
Detrisac CH et al. In vitro culture of cells exfoliated in the urine by patients with diabetes mellitus. J. Clin. Invest. Jan. 1983; 71: 170-173.
Bruno S et al. Isolation and characterization of resident mesenchymal stem cells in human glomeruli. Stem Cells and Development. 2009; 18(6): 867-879.
Ehmann UK et al. Juxtacrine stimulation of normal and malignant human bladder epithelial cell proliferation. J. Urol. Feb. 2001; 167(2 Pt 1): 735-41 Abstract.
Sack GH Jr. et al. Plaque formation and purification of BK virus in cultured human urinary cells. J. gen. virol. 1980; 50: 185-189.
Examination report, EP 08754571.1, dated Jul. 19, 2012.
Wang T et al. Cell-to-cell contact induces mesenchymal stem cell to differentiate into cardiomyocyte and smooth muscle cell. International Journal of Cardiology. 2006; 109: 74-81.
Vesicoureteral Reflux (VUR). UCSF Department of Urology. https://urology.ucsf.edu/patient-care/children/additional/vesicoureteral-reflux. 3 pp.
Lin C-S and Lue TF. Stem cell therapy for stress urinary incontinence: a critical review. Stem Cells and Development. 2012; 21(6): 834-843.
Lee CN et al. Human cord blood stem cell therapy for treatment of stress urinary incontinence. J Korean Med Sci. 2010; 25: 813-6.
Zhang D et al. Urine-derived stem cells: a novel and versatile progenitor source for cell-based therapy and regenerative medicine. Genes & Diseases. Jul. 2, 2014; 1: 8-17.
Wang H-J et al. Development of cellular therapy for the treatment of stress urinary incontinence. Int Urogynecol J. 2011; 22: 1075-1083.
Gräs S and Lose G. The clinical relevance of cell-based therapy for the treatment of stress urinary incontinence. Nordic Federation of Societies of Obstetrics and Gynecology. Acta Obstetricia et Gynecologica Scandinavica. 2011; 90: 815-824.
Staack A and Rodriguez LV. Stem cells for the treatment of urinary incontinence. Curr Urol Rep. 2011; 12: 41-46.
Carr LK et al. Autologous muscle derived cell therapy for stress urinary incontinence: a prospective, dose ranging study. The Journal of Urology. Feb. 2013; 180: 595-601.
Liu G et al. Correction of diabetic erectile dysfunction with adipose derived stem cells modified with the vascular endothelial growth factor gene in a rodent diabetic model. PLOS ONE. Aug. 2013; 8(8): e72790, 13 pp.
Mitterberger M et al. Myoblast and fibroblast therapy for post-prostatectomy urinary incontinence: 1-year followup of 63 patients. The Journal of Urology. Jan. 2008; 179: 226-231.
Yang B et al. Myogenic differentiation of mesenchymal stem cells for muscle regeneration in urinary tract. Chin Med J. 2013; 126(15): 2952-2959.
Chen W et al. Skeletal myogenic differentiation of human urine-derived cells as a potential source for skeletal muscle regeneration. J Tissue Eng Regen Med. 2014; DOI: 10.1002/term.1914.
Liu GH et al. Skeletal myogenic differentiation of urine-derived stem cells and angiogenesis using microbeads loaded with growth factors. Biomaterials. Jan. 2013; 34(4): 1311-1326.
Ouyang B et al. Human urine-derived stem cells alone or genetically-modified with FGF2 improve type 2 diabetic erectile dysfunction in a rat model. PLoS One. Mar. 2014:9(3) e92825.
Liu G et al. Chapter 2: Urine derived stem cells: biological characterization and the potential clinic application. Turksen Kursad (ed.), Stem Cells: Current Challenges and New Directions, Stem Cell Biology and Regenerative Medicine 33. Springer. 2013, pp. 19-28.
Shi Y et al. Chapter 31: Cell therapy and muscle regeneration: Skeletal myogenic differentiation of urine-derived stem cells for potential use in treatment of urinary incontinence. Regenerative Medicine and Tissue Engineering. InTech. 2013, 787-793.
Lin C-S. Advances in stem cell therapy for erectile dysfunction. Advances in Andrology. vol. 2014 (2014), Article ID 140618,10 pages. Abstract only.
Inquiry, Japanese Patent Application No. 2010-509363, dispatched Dec. 24, 2014.
Ono Y et al. Isolation and culture of tubular epithelial progenitor cells from cells in urine samples of a canine model of ischemia/reperfusion, and their potential use for the treatment of renal failure. Report for Health and Labour Sciences Research Grants from 2005 to 2006, Mar. 2006, pp. 31-33. Translation of relevant portions.
Kucia M et al. A population of very small embryonic-like (VSEL) CXCR4+SSEA-1+Oct-4+ stem cells identified in adult bone marrow. Leukemia. 2006; 20: 857-869.
Bowman's Capsule. Wikipedia. 5 pages downloaded Jun. 29, 2016.
Grens K. Putting the pee in pluripotency. The Scientist Magazine. Apr. 1, 2016. 4 pages.
Slough Off definition. The Free Dictionary. 3 pages downloaded Jun. 29, 2016. http:www.thefreedictionary.com/slough+off.
Bharadwaj S et al. Characterization of urine-derived stem cells obtained from upper urinary tract for use in cell-based urological tissue engineering. Tissue Engineering: Part A. 2011; 17(15-16): 2123-2132.
Bharadwaj S et al. Multipotential differentiation of human urine-derived stem cells: potential for therapeutic applications in urology. Stem Cells. 2013; 31: 1840-1856.
Bodin A et al. Tissue-engineered conduit using urine-derived stem cells seeded bacterial cellulose polymer in urinary reconstruction and diversion. Biomaterials. 2010, 31: 8889-8901.
Fischer U et al. Pulmonary Passage is a Major Obstacle for Intravenous Stem Cell Delivery: The Pulmonary First-Pass Effect. Stem Cells and Development. 2009, 18(5): 683-691.
Lang R et al. Self-renewal and differentiation capacity of urine-derived stem cells after urine preservation for 24 hours. PLOS ONE. Jan. 2013; 8(1): e53980, 11 pages.
Liu G et al. Skeletal myogenic differentiation of urine-derived stem cells and angiogenesis using microbeads loaded with growth factors. Biomaterials (2012), http://dx.doi.org/10.1016/j.biomaterials.2012.10.038.
Liu G et al. The effect of urine-derived stem cells expressing VEGF loaded in collagen hydrogels on myogenesis and innervation following after subcutaneous implantation in nude mice. Biomaterials (2013), http://dx.doi.org/10.1016/j.biomaterials.2013.07.077.

(56) References Cited

OTHER PUBLICATIONS

Wu S et al. Implantation of Autologous Urine Derived Stem Cells Expressing Vascular Endothelial Growth Factor for Potential Use in Genitourinary Reconstruction. The Journal of Urology. 2011, 186: 640-647.

Wu S et al. Human urine-derived stem cells seeded in a modified 3D porous small intestinal submucosa scaffold for urethral tissue engineering. Biomaterials. 2011; 32: 1317-1326.

Zhang Y et al. Urine Derived Cells are a Potential Source for Urological Tissue Reconstruction. The Journal of Urology. 2008, 180: 2226-2233.

Zonta S et al. Which Is the Most Suitable and Effective Route of Administration for Mesenchymal Stem Cell-Based Immunomodulation Therapy in Experimental Kidney Transplantation: Endovenous or Arterial? Transplantation Proceedings. 2010, 42: 1336-1340.

Fossum M et al. Isolation and in vitro cultivation of human urothelial cells from bladder washings of adult patients and children. Scandinavian Journal of Plastic and Reconstructive Surgery and Hand Surgery. 2003; 37(1): 41-45.

Fossum M et al. Long-term culture of human urothelial cells—a qualitative analysis. Scandinavian Journal of Plastic and Reconstructive Surgery and Hand Surgery. 2005; 18(1): 11-22.

\* cited by examiner

PROGENITOR CELLS FROM URINE AND METHODS FOR USING THE SAME

RELATED APPLICATIONS

This application is a 35 U.S.C. § 371 national phase application of PCT Application PCT/US2008/006438, filed May 20, 2008, and published in English on Dec. 18, 2008, as International Publication No. WO 2008/153685, and which claims the benefit under 35 U.S.C. § 119(e) of U.S. Provisional Patent Application Ser. No. 60/939,247, filed May 21, 2007, and U.S. Provisional Patent Application Ser. No. 60/943,215, filed Jun. 11, 2007, the disclosure of each of which is incorporated herein by reference in its entirety.

FIELD OF THE INVENTION

This invention relates generally to the isolation of cells from urine, cells isolated and methods of use of the same.

BACKGROUND OF THE INVENTION

Regenerative medicine is an applied field of tissue engineering that focuses on the regeneration of damaged tissues of the body. Applications of regenerative medicine include the reconstruction or replacement of organs such as the bladder.

Many diseases and injuries can lead to damage or loss of the bladder, requiring repair or replacement of the organ. Children with congenital abnormalities such as bladder exstrophy, posterior urethral valves, or myelomeningocele (commonly known as spina bifida) can develop high-pressure and hypertonic low-compliant bladders. In the adult population, bladder cancer is the fourth most commonly diagnosed malignancy in men and the ninth most commonly diagnosed malignancy in women in the United States.

The fundamental function of the bladder is to provide a capacious reservoir that can store urine under low pressure and empty under volitional control. Patients suffering from afflictions that involve a loss of bladder function experience a dramatic, negative alteration in their quality of life, and are at risk for hydronephrosis and renal failure.

Bladder reconstruction, or cystoplasty, is often indicated when drug treatments are inadequate. Currently, augmentation cystoplasty is usually accomplished by placing a detubularized segment of intestine onto the bladder. Although functional, several complications can arise from using intestinal segments or gastric flaps for urinary reconstruction. Deleterious side effects include infection, intestinal obstruction, mucus production, electrolyte abnormalities, perforation, and carcinogenicity. Therefore a more clinically applicable process of bladder reconstruction through tissue-engineered regeneration is needed.

Advances in tissue engineering have demonstrated that bladder regeneration is possible through the use of biodegradable membranes seeded with primary cultured cells (Kropp, et al. (1996) *J. Urol.* 156:599; Atala, et al. (1992) *J. Urol.* 148:658; Oberpenning, et al. (1999) *Nat. Biotechnol.* 17:149). The feasibility of this concept has been demonstrated in humans, and bladder regeneration and the enlargement of bladder volume were accomplished (Atala et al. (2006) *The Lancet* 367:1241-46).

Biomaterial scaffolds that have been used to achieve successful bladder regeneration include acellular collagen matrixes and synthetic polymers. Collagen matrixes include porcine bladder submucosa membrane (BSM) and small intestine submucosa (SIS), which both contain numerous natural components required for normal cell growth, differentiation, and functioning, including collagen, glycoproteins, proteoglycans, and functional growth factors (Hodde, et al. (2001) *Endothelium* 8:11; Voytik-Harbin, et al. (1997) *J. Cell. Biochem.* 67:478). Synthetic polymers scaffolds include polyglycolic acid (PGA), polylactic acid (PLA) and polylactic-co-glucolic acid (PLGA) (Oberpenning, et al. (1999) *Nat. Biotechnol.* 17:149; Atala, et al. (1993) *J. Urol.* 150:608).

Autologous bladder cells are the most commonly used cell source for tissue engineered constructs in patients who do not have cancer. A patient's own cultured cells seeded onto a bio-material scaffold can act as a framework for regenerating tissues. To obtain the bladder cells, however, invasive tissue biopsy procedures are performed for cell harvest, which increase medical care expenditures and are associated with potential complications such as bleeding, infection, and urethral or bladder injury. In addition, cells obtained from bladder biopsy sometimes fail to grow due to mucosa tissue disruption before or during biopsy (Zhang & Frey (2003) *Adv. Exp. Med. Biol.* 539:907).

Alternative cell sources are being investigated for urologic reconstruction, including embryonic, fetal and adult stem cells. Stem cells are self-renewing and not terminally differentiated, and therefore can produce various types of cells. Human embryonic stem cells are promising for tissue engineering purposes (Frimberger, et al. (2005) *Urology* 65:827; Lakshmanan, et al. (2005) *Urology* 65:821), but questions of immunocompatibility, tumor formation, and ethics remain. Fetal or adult stem cells are found only in very sparse numbers in the host tissue, may not expand well in culture, and have a more restricted differentiation potential (Vogel (2001) *Science* 292:1820). Therefore, current clinical use for stem cells in tissue engineering may be limited.

More preferable alternatives to autologous cell harvest through biopsy are needed for urological tissue engineering and cell therapy, particularly where autologous cells are not available for biopsy.

SUMMARY OF THE INVENTION

Provided herein are methods for producing a culture of urine progenitor cells (UPCs), including providing a urine sample; and then isolating urine progenitor cells from said urine sample. In some embodiments said isolating step is carried out by: (a) collecting cells from a urine sample to provide a crude cell sample; and (b) selecting urine progenitor cells from said crude cell sample. In some embodiments said collecting step is carried out by centrifugation of said urine sample.

In some embodiments, selecting is carried out by plating said cells in a composition comprising a selective cell medium. In some embodiments, selecting is carried out based upon morphology. In some embodiments, selecting is carried out by selecting a marker specific to urine progenitor cells, e.g., C-kit (CD117), SSEA-4, CD105, CD73, CD90, CD133, and/or CD44. In some embodiments, urine progenitor cells are from a mammalian subject (e.g., a human subject). Urine progenitor cells produced by any of the methods disclosed herein are another aspect of the present invention.

Also provided is an isolated urine progenitor cell, wherein said cell is c-kit positive, and wherein said cell can differentiate into two or more lineages selected from the group consisting of: urothelium, smooth muscle, endothelium and interstitial cells.

Methods of seeding cells onto a tissue scaffold are provided, including providing UPCs, differentiating UPCs and seeding the differentiated cells onto a biodegradable tissue scaffold. Tissue scaffolds may comprises a collagen matrix and/or a synthetic polymer such as polyglycolic acid (PGA), polylactic acid (PLA) or polylactic-co-glucolic acid (PLGA).

Methods of treating a subject in need thereof are provided, including providing a bladder tissue substrate, wherein said substrate comprises differentiated UPCs; and transplanting the substrate into the patient. Substrates may include a collagen matrix and/or a synthetic polymer such as polyglycolic acid (PGA), polylactic acid (PLA) or polylactic-co-glucolic acid (PLGA).

Kits are provided that may include a container suitable for the transport of a urine sample; media; one or more antibiotics; a package for holding said container, media, and antibiotics; and optionally, instructions for use.

A further aspect of the present invention is the use of cells as described above for the preparation of a medicament for carrying out a method of treatment as described above.

The foregoing and other objects and aspects of the present invention are explained in greater detail in the drawings herein and the specification set forth below.

DETAILED DESCRIPTION OF THE PREFERRED EMBODIMENTS

Figure 1:
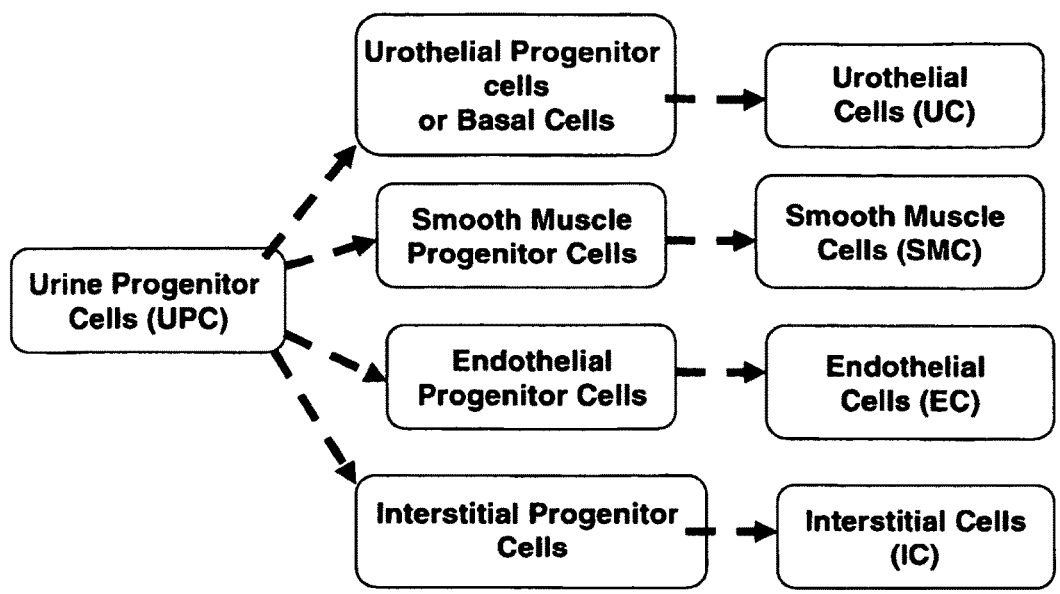
FIG. 1. Diagram of proposed route of urine progenitor cell (UPC) differentiation.

The present invention concerns progenitor cells and methods of selecting and culturing progenitor cells from urine. Advantageously, cells found in urine may be obtained without the need for a tissue biopsy, saving the patient discomfort and possible complications.

The disclosures of all cited United States Patent references are hereby incorporated by reference to the extent that they are consistent with the disclosures herein. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" and "/" refer to and encompass any and all possible combinations of one or more of the associated listed items, as well as the lack of combinations when interpreted in the alternative ("or").

"Urine progenitor cells" or "UPCs" are cells collected and/or isolated from urine that possess both pluripotency and proliferative potential. A UPC is "pluripotent" in that it is capable of giving rise to various cell types within one or more lineages. For example, UPCs according to some embodiments possess the potential to differentiate into one or more of the following: bladder urothelial, smooth muscle, endothelium, interstitial cells, and even bone, muscle, epithelial cells and other types of cells and tissues. Previous studies have shown that urothelial cells can differentiate into mature chondrocytes (Fernandez-Conde, *Bone* (1996) 18(3): 289-91).

The cells sloughed from the urinary tract lumen are generally believed to be old or damaged superficial cells that are difficult to culture and maintain in vitro. A few cells obtained from urine can grow rapidly on feeding layer cells. However, feeding layer cells are usually derived from embryonic mouse tissues that might transfer viruses from animal to human when human cells are cultured with the mouse feeder cells. To avoid this complication, we have recently grown cells from urine without feeding layer cells. Cells were obtained that possessed progenitor cell features and retained proliferative capability and pluripotency potential.

Our studies indicate that there are mixed cell populations in urine: progenitor cells and mature cells as well. As disclosed herein, urine contains urothelial progenitor cells and smooth muscle progenitor cells, as well as endothelial and interstitial progenitor cells. Progenitor cells that are found in urine may originate from bladder tissue, renal tissue, etc. In some embodiments, UPCs undergo selection against cells of renal origin. This can be accomplished by, for example, passaging the collected cells, as it is thought that renal cells generally do not survive passaging. In some embodiments UPCs well double upon growing between 24-48 hours (e.g., every 31.3 hours), allowing them to be grown in large quantities. In further embodiments, UPCs do not induce tumor formation, and in some embodiments UPCs do not require feeder cells for growth or differentiation.

"Isolated" signifies that the cells are placed into conditions other than their natural environment. However, the term "isolated" does not preclude the later use of these cells thereafter in combinations or mixtures with other cells.

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric.

Subjects may also include animal subjects, particularly mammalian subjects such as canines, felines, bovines, caprines, equines, ovines, porcines, rodents (e.g., rats and mice), lagomorphs, primates (including non-human primates), etc., for, e.g., veterinary medicine and/or pharmaceutical drug development purposes.

Collection of Cells.

UPCs may be collected from any animal that produces urine, including humans. In some embodiments of the present invention, urine progenitor cells are collected from the urine of a mammal. For example, UPCs may be collected from the urine of a dog, cat, pig, cow, horse, monkey or human. In particular embodiments, urine progenitor cells are obtained from the urine of a human.

In some embodiments, UPCs are collected from samples of fresh spontaneous urine, or drainaged urine through a urethral catheter or from a bladder wash. Urine samples can be centrifuged at 1500 RPM for 5 minutes at 4° C., the supernatant aspirated and cells washed with a suitable solution such as phosphate-buffered saline (PBS). The PBS may optionally contain 5% fetal bovine serum (FBS) and 1% penicillin-streptomycin to protect cells from injury and potential infection, respectively.

Further examples of methods and apparatuses for isolating cells from biological fluids may be found in, e.g., U.S. Pat. No. 5,912,116; U.S. Patent Application No. 20040087017; U.S. Patent Application No. 20020012953; and WO 2005/047529.

Selection and Propagation of Cells.

In some embodiments, collected UPCs are expanded. "Expanding" refers to an increase in number of viable cells. Expanding may be accomplished by, e.g., growing the cells through one or more cell cycles wherein at least a portion of the cells divide to produce additional cells.

The "primary culture" is the first culture to become established after seeding collected cells into a culture vessel. "Passaging" refers to the transfer or subculture of a culture to a second culture vessel, usually implying mechanical or enzymatic disaggregation, reseeding, and often division into two or more daughter cultures, depending upon the rate of proliferation. If the population is selected for a particular genotype or phenotype, the culture becomes a "cell strain" upon subculture, i.e., the culture is homogeneous and possesses desirable characteristics. The establishment of "cell lines," as opposed to cell strains, are by and large undifferentiated, though they may be committed to a particular lineage.

"Selection" can be based upon any unique properties that distinguish one cell type from another, e.g., density, size, unique markers, unique metabolic pathways, nutritional requirements, protein expression, protein excretion, etc. For example, cells may be selected based on density and size with the use of centrifugal gradients. Unique markers may be selected with fluorescent-activated cell sorting (FACS), immunomagnetic bead sorting, magnetic activated cell sorting (MACS), panning, etc. Unique metabolic pathways and nutritional requirements may be exploited by varying the makeup and/or quantity of nutritional ingredients of the medium on which cells are grown, particularly in a serum-free environment. Protein expression and/or excretion may be detected with various assays, e.g., ELISA.

In some embodiments, UPCs are selected by providing cells isolated from urine in a particular growing environment that promotes the growth of progenitor cells, such as progenitor cell medium. In some embodiments, the progenitor cell medium contains 3/4 DMEM, 1/4 Ham's F12, 10% FBS, 0.4 mg/ml hydrocortisone, $10^{-10}$ M, Chron Toxin, 5 mg/ml, insulin, 1.2 mg/ml adenine, 2.5 mg/ml transferrin plus 0.136 mg/ml 3,39,5-triiodo-L-thyronine, 10 mg/ml EGF, and 1% penicillin-streptomycin (Zhang et al., In vitro Cell Dev. Biol.-Animal 37:419, 2001). In further embodiments, isolated UPCs are provided in a particular growing environment that promotes the selective differentiation of the progenitor cells. For example, in some embodiments UPCs grown in keratinocyte serum free medium develop into urothelium. In further embodiments, UPCs grown in DMEM with 10% fetal bovine serum develop into smooth muscle-like cells. In some embodiments, endothelial-like cells may be cultured in M199 with 20% FBS, 2 mmol/l L-glutamine, EGF (5 nl/ml) 1% sodium pyruvate and 1% penicillin-streptomycin. In some embodiments, interstitial-like cells may be cultured in DMEM with 10% FBS, 2 mmol/l L-glutamine, and 1% penicillin-streptomycin.

Figure 6:
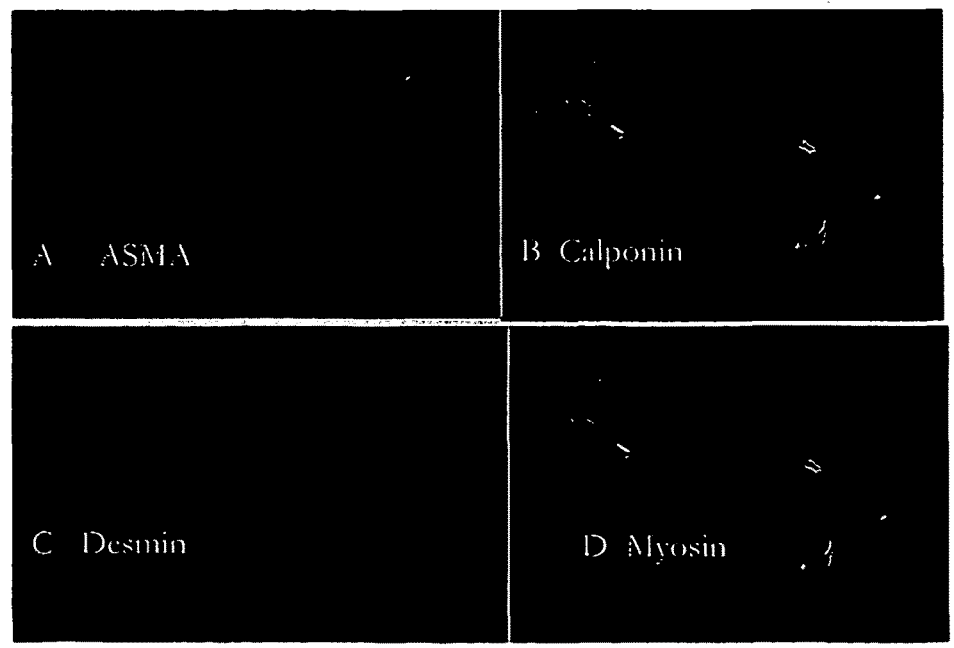
FIG. 6. Microscopy images of UPCs double stained for nucleic acids and markers specific to smooth muscle. The images show that urine-derived smooth muscle progenitor cells express smooth muscle protein markers such as alpha-smooth muscle actin (ASMA) (A), Calponin (B), Desmin (C) and Myosin (D).
Figure 7:
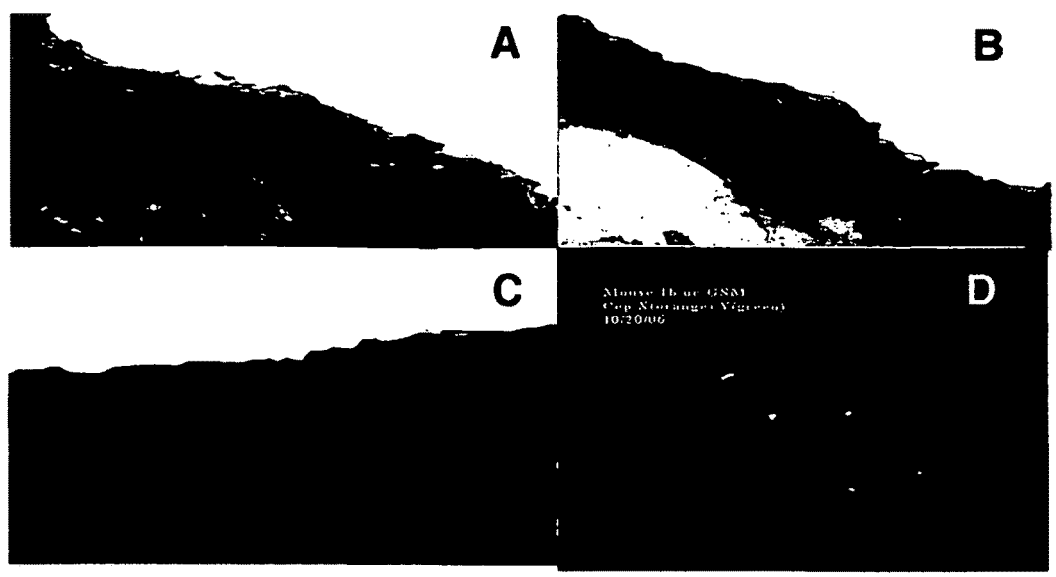
FIG. 7. Histological features of UPC-bladder submucosa membrane (BSM) and UPC-small intestine submucosa (SIS) constructs one month after implantation in vivo. A. Masson Trichrome staining and detection of UPCs grown on SIS scaffolds. B. LacZ-labeled UPC identified on SIS matrix. C. Hematoxylin & Eosin (H&E) stained sections of urine cell-seeded BSM grafts. D. Human X/Y chromosomes of UPC were noted within the BSM matrix.
Figure 8:
FIG. 8. Four cells types observed in cultured urine cells: endothelial-like, smooth muscle-like, epithelial-like and interstitial-like cells.
Figure 9:
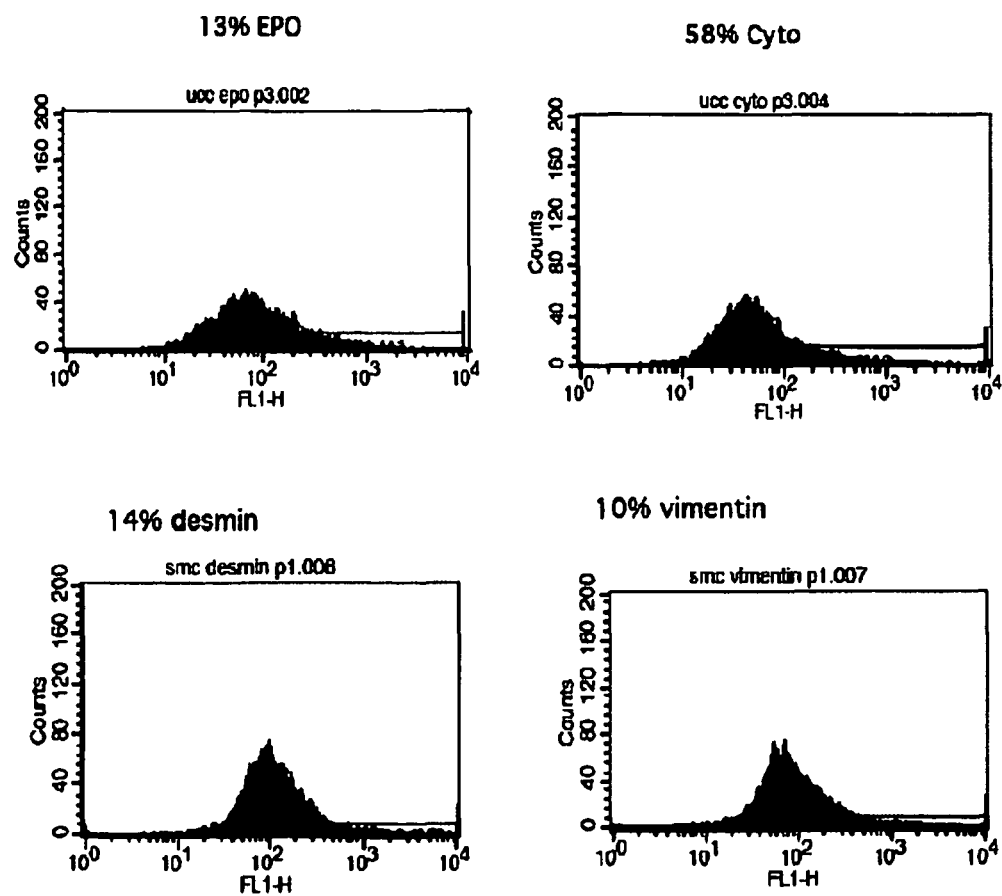
FIG. 9. Cells were analyzed by FACS for cell-specific markers AE1/AE3, Desmin, Vimentin and Erythropoietin.
Figure 10:
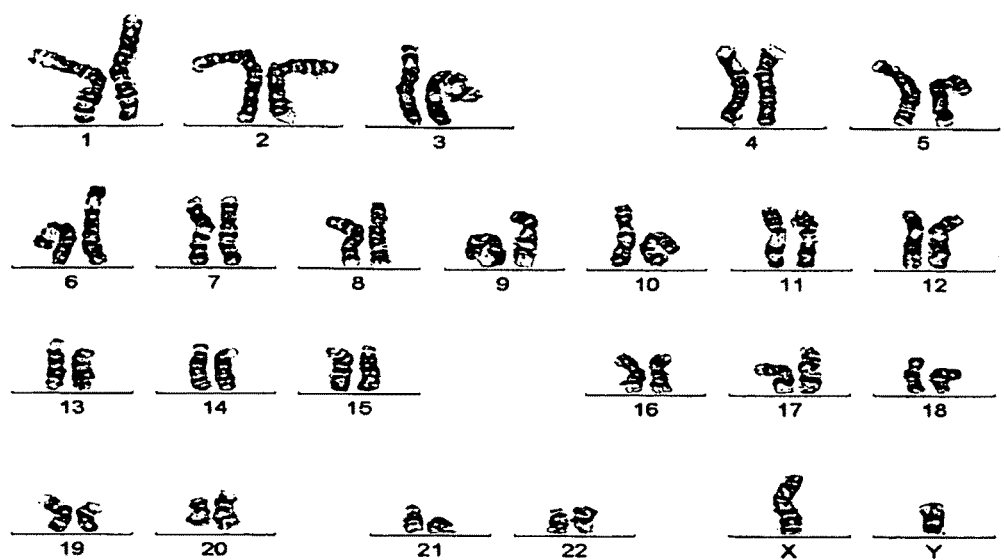
FIG. 10. Giemsa band karyogram of clonal UPCs shows normal chromosome patterns on passage 6.

In other embodiments, UPCs are selected by morphology. For example, cells isolated from urine may be diluted to a concentration allowing for the isolation of single cells (e.g., cells can be diluted to a concentration of approximately 0.5 cells/well in a multi-well plate), and observed under a microscope. Wells containing single cells can be retained for expansion, and selected by observed morphology, e.g., urothelium, smooth muscle, endothelium and/or interstitial cells (See FIG. 6A).

Urine progenitor cells according to some embodiments of the present invention can be identified, selected, and/or isolated based on one or more "markers." Such markers include specific gene expression, antigenic molecules found on the surface of such cells, etc. In particular embodiments, urine progenitor cells are selected and isolated based upon the expression of at least one specific maker. In some embodiments, UPCs have one or more of the following markers such as CD117 (C-kit), SSEA-4, CD105, CD73, CD90, CD133, and CD44, and do not have an appreciable amount of one or more of the following markers: CD31, CD34, and CD45. Accordingly, certain embodiments embrace selecting and isolating urine progenitor cells which express one or more of CD117, SSEA-4, CD105, CD73, CD90, CD133, and CD44 and/or lack expression of one or more of CD31, CD34, and CD45. For example, in some embodiments a urine progenitor cell of the present invention is identified, selected, and/or isolated based on the expression of CD117.

In some embodiments UPCs can be obtained as disclosed herein by collecting cells from a urine sample, e.g., by centrifugation, and/or directly plating the cells in or on a suitable medium, and/or selecting and isolating urine progenitor cells based upon progenitor-specific cell marker expression (e.g., via immunohistochemistry or western blot analysis). Alternatively, urine progenitor cells may be obtained by collecting and selecting cells via fluorescence-activated cell sorting, e.g., using a marker-specific antibody (e.g., anti-CD117 antibody) conjugated to a fluorophore (e.g., APC, phycoerythrin, allophycocyanins, fluorescein, TEXAS RED, etc.), or magnetic selection using a marker-specific antibody conjugated to magnetic particles. By way of illustration, cells may be incubated with a rabbit polyclonal antibody that specifically binds to the extracellular domain (amino acids 23-322) of the CD117 receptor protein (De Coppi, et al. (2007) Nat. Biotechnol. 25:100). The CD117-positive cells can be purified by incubation with magnetic Goat Anti-Rabbit IgG MicroBeads and selected on a Mini-MACS apparatus. Urine progenitor cells may also be selected with a monoclonal anti-CD117 antibody directly conjugated to MicroBeads. Any suitable method for selection including attachment to and disattachment from a solid phase is contemplated within the scope of the invention.

Urine progenitor cells according to some embodiments of the present invention can be routinely passaged or subcultured, e.g., by a 1:4 dilution and permitted to expand to about 50-70% confluency. Isolated populations of urine progenitor cells can be routinely grown and maintained under conventional culture conditions, e.g., a humidified atmosphere of 5% $CO_2$ at 37° C. While cells of the invention can be grown in complex media with KFSM-Progenitor cell medium (1:1) (Zhang et al., *In vitro Cell Dev. Biol.-Animal* 37:419, 2001), it will generally be preferable that the cells be maintained in a simple serum-free medium such as KSFM for urothelial progenitor cells, or medium with 10% FBS for smooth muscle or interstitial progenitor cells such as Dulbecco's Minimal Essential Media (DMEM), Hank's Basic Salt Solution (HBSS), Dulbecco's phosphate-buffered saline (DPBS), RPMI, or Iscove's-modified Dulbecco's medium (IMDM), in order to effect more precise control over the differentiation of the progenitor cell into the desired cell. Clone urine progenitor cell lines can also be generated by a conventional limiting dilution method either in 96-well plates or 24-well plates. Once cell colonies form, the cells are detached and transferred into multi-well dishes.

In some embodiments, growth factors or other mitogenic agents are included in the media to promote proliferation and differentiation of distinct populations of cells. In this regard, particular embodiments of the invention embrace culturing urine progenitor cells with selective medium that supports the growth and differentiation of the urine progenitor cells into urothelial, smooth muscle, interstitial cells, etc. Differentiation in the present context refers to a status of cells in which the cells develop specific morphological or functional properties. By way of illustration, when urine progenitor cells are grown in keratinocyte serum-free medium (KSFM) supplemented with 0.09 mM calcium, the cells differentiate into urothelium. Likewise, urine progenitor cells cultured in DMEM supplemented with serum, e.g., 10% fetal bovine serum (FBS) promotes differentiation into smooth muscle cells. Accordingly, the present invention also embraces populations of urine progenitor cells which are differentiated and express at least one urothelial-specific marker or at least one smooth muscle-specific marker, or at least one other tissue-specific marker (e.g., interstitial-specific).

Determination of whether a UPC has differentiated into a specific type of cell can be achieved by the detection of markers specific to these cell types. For example, urothelial cells can be identified by the presence of one or more of urothelial-specific markers including, e.g., uroplakin, cytokeratin 7, cytokeratin 13, cytokeratin 17, and cytokeratin 19 and cytokeratin 20; whereas smooth muscle cells can be identified by the presence of one or more smooth muscle-specific markers including, e.g., alpha-smooth muscle actin, desmin, calponin and myosin. Cell type-specific marker expression can be determined using any suitable conventional method include, e.g., immunohistochemistry and/or western blot analyses.

Moreover, if desired, the cells can be frozen or cryopreserved prior to use, and then thawed to a viable form. Methods of freezing or cryopreserving cells (for subsequent return to viable form) are well known in the art. For example, cryopreservation of cells can involve freezing the cells in a mixture of a growth medium and another liquid that prevents water from forming ice crystals, and then storing the cells at liquid nitrogen temperatures (e.g., from about −80 to about −196° C.). See, e.g., U.S. Pat. No. 6,783,964.

Methods of Treatment.

Diseases that may be treated with the methods disclosed herein include, but are not limited to, augmentation or replacement of urinary tract tissues. "Treat" as used herein refers to any type of treatment that imparts a benefit to a patient, e.g., a patient afflicted with or at risk for developing a disease. Treating includes actions taken and actions refrained from being taken for the purpose of improving the condition of the patient (e.g., the relief of one or more symptoms), delay in the onset or progression of the disease, etc.

Having demonstrated that urine progenitor cells according to some embodiments of the present invention can differentiate into various functional cells types, the urine progenitor cells of the present invention find application in treating diseases and conditions of the urinary tract including, e.g., bladder exstrophy; bladder volume insufficiency; reconstruction of bladder following partial or total cystectomy; repair of bladders, kidneys or ureters damaged by trauma; and the like. Treatment in accordance with some embodiment involve urinary tract diseases and conditions such as congenital abnormalities, cancer, trauma, radiation, infection, iatrogenic injures, nerve injury or other causes. Generally, treatment involves altering urinary tract function; improving urinary tract function; or reconstructing, repairing, augmenting, or replacing damaged urinary tract cells or whole tissues or organs to prevent or treat diseases or conditions of the urinary tract. In this regard, urine progenitor cells can be used in tissue engineering of urinary tract structures such as ureters, bladders, urethra, renal pelvic, kidney, bone, cartilage, muscle, skin, and the like.

Furthermore, urine progenitor cells may find application in pharmacology of lower urinary tract and diagnosis of urinary tract diseases. Cells according to some embodiments of the present invention can be used to diagnose diseases such as hematuria or tumors in the urinary tract system, e.g., tumors of the bladder, renal pelvic, kidney, ureters, prostate gland and urethra; renal diseases such as renal diabetes, renal tubule necrosis, acute or chronic renal failure, and renal rejection after renal transplantation; and other, diseases including interstitial cystitis, neuropathic bladder, irradiated bladder, and vesicoureteral reflux or reflux nephropathy. See, e.g., U.S. Pat. Nos. 5,733,739, 5,325,169 and 5,741,648.

In accordance with the present invention, in some embodiments treatment involves administration of an effective amount of urine progenitor cells, e.g., undifferentiated, differentiated or mixtures thereof, to a subject in need of treatment thereby ameliorating or alleviating at least one sign or symptom of the disease or condition of the subject.

In applications where tissues are implanted, in some embodiments cells are of the same species as the subject into which the tissue is to be implanted. In some embodiments cells are autogeneic (i.e., from the subject to be treated), isogeneic (i.e., a genetically identical but different subject, e.g., from an identical twin), allogeneic (i.e., from a non-genetically identical member of the same species) or xenogeneic (i.e., from a member of a different species).

In some embodiments, when cells of the invention are used for treating a subject, the cells are formulated into a pharmaceutical composition containing the cells in admixture with a pharmaceutically acceptable vehicle or carrier. Such formulations can be prepared using techniques well known in the art. See, e.g., U.S. Patent Application 2003/

0180289; Remington: *The Science and Practice of Pharmacy*, Alfonso R. Gennaro, editor, 20th ed. Lippincott Williams & Wilkins: Philadelphia, Pa., 2000. In the manufacture of a pharmaceutical formulation according to the invention, the cells are typically admixed with, inter alia, an acceptable carrier. The carrier must, of course, be acceptable in the sense of being compatible with any other ingredients in the formulation and must not be deleterious to the patient. The carrier may be a solid or a liquid, or both (e.g., hydrogels), and can be formulated with the cells as a unit-dose formulation. In one embodiment the cells are provided as a suspension in the carrier to reduce clumping of the cells.

In another embodiment, the cells are formulated in an encapsulated form (e.g., encapsulated in a capsule that is permeable to nutrients and oxygen to sustain the viability of the cells in vivo). Materials and methods for the encapsulation of cells in permeable capsules are well known and described in, for example, U.S. Pat. No. 6,783,964. For example, the cells may be encapsulated in a microcapsule of from 50 or 100 μm to 1 or 2 mm in diameter that comprises an internal cell-containing core of polysaccharide gum surrounded by a semipermeable membrane; a microcapsule that comprises alginate in combination with polylysine, polyornithine, and combinations thereof. Other suitable encapsulating materials include, but are not limited to, those described in U.S. Pat. No. 5,702,444.

In a particular embodiment, the cells of the present invention are administered with a biodegradable scaffold or matrix. It has been demonstrated that the bladder cells can form normal bladder structures of distinctive layers with urothelium growing on the top of smooth muscle cells after in vitro co-culture on collagen-rich scaffolds (Zhang, et al. (2000) *J. Urol.* 164:928). Additionally, bladder cell-seeded scaffold constructs have been shown to take part in the regenerating process of tissue remodeling in a partial cystostomy model (Zhang, et al. (2005) *BJU Int.* 96:1120). Therefore, embodiments of progenitor cells find application in engineering cell-scaffold constructs in vitro for later in vivo implantation to completely regenerate the bladder.

A biodegradable scaffold or matrix is any substance not having toxic or injurious effects on biological function and is capable of being broken down into its elemental components by a host. Desirably, the scaffold or matrix is porous to allow for cell deposition both on and in the pores of the matrix, and in certain embodiments, is shaped. Such formulations can be prepared by supplying at least one cell population to a biodegradable scaffold to seed the cell population on and/or into the scaffold. In some embodiments the seeded scaffold is then implanted in the body of the recipient subject where the separate, laminarily organized cell populations facilitate the formation of neo-organs or tissue structures.

Biodegradable scaffolds that may be used include, e.g., natural or synthetic polymers, such as collagen (e.g., SIS and BSM), poly(alpha esters) such as poly(lactate acid), poly(glycolic acid), polyorthoesters and polyanhydrides and their copolymers, which can be degraded by hydrolysis at a controlled rate and are reabsorbed. Examples of other suitable materials are provided in U.S. Pat. No. 7,186,554.

The biodegradable scaffold can be "shaped" using methods such as, for example, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape that resembles the final form. Next, a solvent is used to dissolve away one of the components, resulting in pore formation (see U.S. Pat. No. 5,514,378). In nucleation, thin films in the shape of a reconstructive urothelial graft are exposed to radioactive fission products that create tracks of radiation damaged material. Next the polycarbonate sheets are etched with acid or base, turning the tracks of radiation-damaged material into pores. Finally, a laser may be used to shape and burn individual holes through many materials to form a reconstructive urothelial graft structure with uniform pore sizes. These shaping techniques may be employed in combination. For example, a biodegradable matrix can be weaved, compression molded and also glued. Furthermore, different polymeric materials shaped by different processes may be joined together to form a composite shape. The composite shape can be a laminar structure. For example, a polymeric matrix can be attached to one or more polymeric matrixes to form a multilayer polymeric matrix structure. The attachment can be performed by gluing with a liquid polymer or by suturing. In addition, the polymeric matrix can be formed as a solid block and shaped by laser or other standard machining techniques to its desired final form. Laser shaping refers to the process of removing materials using a laser.

The biodegradable scaffold can be treated with additives or drugs prior to implantation (before or after it is seeded with cells), e.g., to promote the formation of new tissue after implantation. Thus, for example, growth factors, cytokines, extracellular matrix components, and/or other bioactive materials can be added to the biodegradable scaffold to promote graft healing and the formation of new tissue. Such additives will, in general, be selected according to the tissue or organ being reconstructed or augmented, to ensure that appropriate new tissue is formed in the engrafted organ or tissue. For examples of such additives for use in promoting bone healing, see, e.g., Kirker-Head (1995) *Vet. Surg.* 24 (5):408-19.

Seeding of cells onto the biodegradable scaffold may be performed according to standard methods. For example, the seeding of cells onto polymeric substrates for use in tissue repair has been reported (see, e.g., U.S. Pat. No. 6,171,344 to Atala, which is incorporated by reference herein; Atala, et al. (1992) *J. Urol.* 148:658-62; Atala, et al. (1993) *J. Urol.* 150:608-12). As an example, cells grown in culture can be trypsinized to separate the cells, and the separated cells can be seeded on the biodegradable scaffold. Alternatively, cells obtained from cell culture can be lifted from a culture plate as a cell layer, and the cell layer can be directly seeded onto the biodegradable scaffold without prior separation of the cells.

The density of cells seeded onto the biodegradable scaffold can be varied. For example, in some embodiments greater cell densities promote greater tissue formation by the seeded cells, while lesser densities can permit relatively greater formation of tissue by cells infiltrating the graft from the host. Other seeding techniques can also be used depending on the biodegradable scaffold and the cells. For example, the cells can be applied to the biodegradable scaffold by vacuum filtration. Selection of cell types and seeding cells onto a biodegradable scaffold will be routine to one of ordinary skill in the art in light of the teachings herein.

In further embodiments, formulations of the invention include those for parenteral administration (e.g., subcutaneous, intramuscular, intradermal, intravenous, intraarterial, intraperitoneal injection) or implantation. In some embodiments, administration is carried out intravascularly, either by simple injection, or by injection through a catheter positioned in a suitable blood vessel, such as a renal artery. In another embodiment, administration is carried out as a graft to an organ or tissue to be augmented as discussed above.

Formulations of the present invention suitable for parenteral administration include sterile liquid, preferably aqueous, injection compositions of the cells, which preparations may be isotonic with the blood of the intended recipient. These preparations can also contain anti-oxidants, buffers, bacteriostats and solutes that render the formulation isotonic with the blood of the intended recipient. The preparations are, apart from the cells being administered, sterile in the sense that they are free of microbial contaminants such as bacteria and viruses. The formulations can be in a synringeable, injectable form, can be in a form suitable for surgical implantation, e.g., into the bladder, urethra, ureter, or kidney of a subject, or in any other form suitable for administration into the subject.

According to some embodiments, the cells administered to the subject can be syngeneic (i.e., isologous, including isogeneic and autogeneic), allogeneic (i.e., homologous) or xenogeneic (i.e., heterologous) with respect to the subject being treated, depending upon other steps such as the presence or absence of encapsulation or the administration of immune suppression therapy of the cells.

The therapeutically effective dosage of cells will vary somewhat from subject to subject, and will depend upon factors such as the age, weight, and condition of the subject and the route of delivery. Such dosages can be determined in accordance with procedures known to those skilled in the art. In general, in some embodiments, a dosage of $1\times10^5$, $1\times10^6$ or $5\times10^6$ up to $1\times10^7$, $1\times10^8$ or $1\times10^9$ cells or more per subject may be given, administered together at a single time or given as several subdivided administrations. In other embodiments a dosage of between $1\text{-}100\times10^8$ cells per kilogram subject body weight can be given, administered together at a single time or given as several subdivided administrations. Of course, follow-up administrations may be given if necessary.

If desired or necessary, the subject can also be administered an agent for inhibiting transplant rejection of the administered cells, such as rapamycin, azathioprine, corticosteroids, cyclosporin and/or FK506, in accordance with known techniques. See, e.g., U.S. Pat. Nos. 5,461,058; 5,403,833; and 5,100,899; see also U.S. Pat. Nos. 6,455,518; 6,346,243; and 5,321,043.

Moreover, cells of the present invention can be transfected (e.g., with a specific gene) prior to seeding with genetic material. Useful genetic material may be, for example, genetic sequences that are capable of reducing or eliminating an immune response in the host. For example, the expression of cell surface antigens such as class I and class II histocompatibility antigens can be suppressed. This would allow the transplanted cells to have a reduced chance of rejection by the host.

Kits for Collecting Urine Progenitor Cells.

Kits are also provided herein for the collection of urine samples. Preferably kits according to the present invention serve to preserve the viability of urine progenitor cells during transport to a remote location (e.g., a suitable laboratory facility). In some embodiments, kits include a tube containing a suitable media (e.g., 1-15 mL, and in some embodiments 5 mL of a serum such as fetal bovine serum). The media may be provided frozen, to be thawed before use. In other embodiments, kits include a tube containing antibiotics (e.g., 1-15 mL, and in some embodiments 5 mL of a solution containing 1% penicillin and streptomycin). The antibiotics may be in powder form or in aqueous solution (optionally provided frozen, to be thawed before use).

Kits may also include suitable containers (e.g., bottles) for the collection of urine samples (e.g., three sterile plastic bottles of a suitable volume, e.g., 100-1,000 mL, and in some embodiments 500 mL). Kits may also include alcohol swabs. In some embodiments cooling means such as ice bags, cold packs, etc., are included to keep urine cool at approximately 4° C. (e.g., 2 ice bags having dimensions of 3 inch×2 inc×0.5 inch). Further embodiments include a container that can hold the above listed components (e.g., a plastic box having dimensions of 6 inch tall×6 inch wide×7 inch long), and optionally also includes instructions for use.

The present invention is explained in greater detail in the following non-limiting examples.

Example 1

Isolation and Characterization of Progenitor Cells from Urine

Fifty-eight human urine samples were collected from 22 male and one female donors (15 healthy individuals and 8 patients), ranging in age from 2 to 50 years. No bacterial contamination was found in any cultures. Urine samples were centrifuged at 1500 RPM for 5 minutes at 4° C. and washed two times with sterile PBS. Cells were plated at an average of 0.5 cell/well in multi-well plates with progenitor cell medium using a gradual dilution method. The progenitor cell medium contains 3/4 DMEM, 1/4 Ham's F12, 10% FBS, 0.4 mg/ml hydrocortisone, $10^{-10}$ M, Chron Toxin, 5 mg/ml, insulin, 1.2 mg/ml adenine, 2.5 mg/ml transferrin plus 0.136 mg/ml 3,39,5-triiodo-L-thyronine, 10 mg/ml EGF, and 1% penicillin-streptomycin (Zhang et al., In vitro Cell Dev. Biol.-Animal 37:419, 2001). Single cells were identified and allowed to grow to more than 50% confluence. Cells were subsequently subcultured, transferred to a 6-cm culture dish and expanded.

Figure 2:
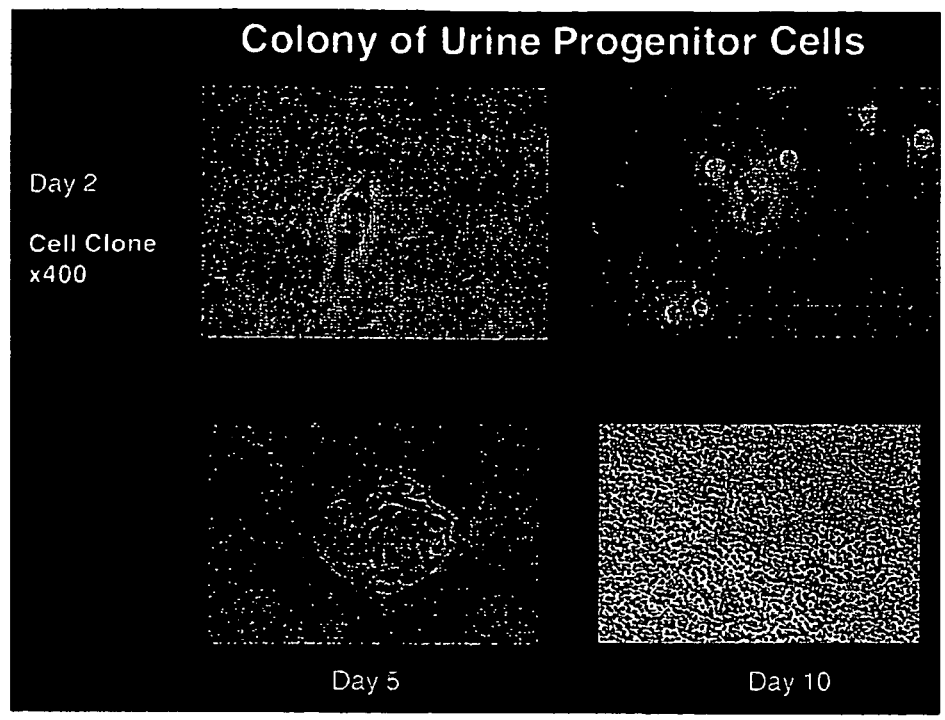
FIG. 2. Microscopy images of progenitor cells from urine that have been cultured in vitro. The cells can proliferate without feeding layer cells.

Primary cell outgrowth was obtained in about 39% of the cultures initiated from urine samples. Average numbers of cells in the colony were 4.5/100 ml urine in healthy individuals on the second day (Table 1 and FIG. 1). The cells were small, brighter-looking cells that were most likely from the base layer of the bladder mucosa and relatively undifferentiated based upon our experience with long-term observation. A consistently high yield of urine cells was achieved from each clonal line. Cell doubling time of urine cells was 31.3 hours in a complex media with progenitor cell medium and KSFM (1:1). It took 10 to 12 days for urine cells from a single cell to reach confluence in a 6-cm culture dish (FIG. 2).

TABLE 1

| Age | Number of Urine Samples | Average of Clone #/100 ml Urine | Percentage of Colony Formation |
|---|---|---|---|
| 2 yrs or younger | 6 | 3.3 | 37% (7/17) |
| 13-40 yrs old | 6 | 5.8 | 50% (8/16) |
| >40 yrs old | 6 | 3.5 | 38% (7/16) |

TABLE 1-continued

| Sources | | Number of Urine Samples | Average of Clone #/100 ml Urine | Percentage of Colony Formation |
|---|---|---|---|---|
| Morning Urine | | 6 | 4.5 | 50% (6/12) |
| Fresh Urine | | 6 | 7.2 | 65% (11/17) |
| Storage at 4° C. | 4 hours | 6 | 2.3 | 38% (3/8) |
| | 8 hours | 6 | 1.2 | 17% (1/6) |
| | 24 hours | 6 | 0.2 | 17% (1/6) |

To demonstrate molecular and cellular features of the urine cells, expression of progenitor cell-specific and differentiated cell-specific markers was analyzed. Urine cells at passage 1, 3 and 4 all stained positively for progenitor cell-specific surface markers, including C-kit, SSEA-4, CD105$^+$, CD73$^+$, CD90$^+$, CD133$^+$, and CD44$^+$ and stained negatively for CD31$^-$, CD34$^-$, and CD45$^-$ (Table 2 and FIG. 3). CD44 is considered a cell surface marker for bladder base cells (Desai, et al. (2000) *Mod. Pathol.* 13:1315). Since base cells have the potential to self-renew and can proliferate and differentiate into intermediate and superficial cells, base cells are referred to as urothelial progenitor cells or stem cells (Staack, et al. (2005) *Differentiation* 73:121). Basal cells in the urine were confirmed by CD44 and immunofluorescence with cytokeratin 13, an intracellular protein marker for the basal and intermediate cell (Romih, et al. (2005) *Cell Tissue Res.* 320:259).

TABLE 2

| CD Antigens | Passage 1 (%) | Passage 3 (%) | Passage 4 (%) |
|---|---|---|---|
| C-kit (CD117) | 7 | 2 | 0.5 |
| SSEA-4 | — | 72 | 75 |
| CD105 | 93 | 86 | 71 |
| CD73 | — | 62 | 41 |
| CD90 | 90 | 83 | 89 |
| CD133 | — | 2 | 10 |
| CD44 | 95 | 67 | 40 |
| CD31 | — | 0.5 | 0 |
| CD34 | 0 | 0 | 0 |
| CD45 | — | 1 | 0.5 |

Figure 3:
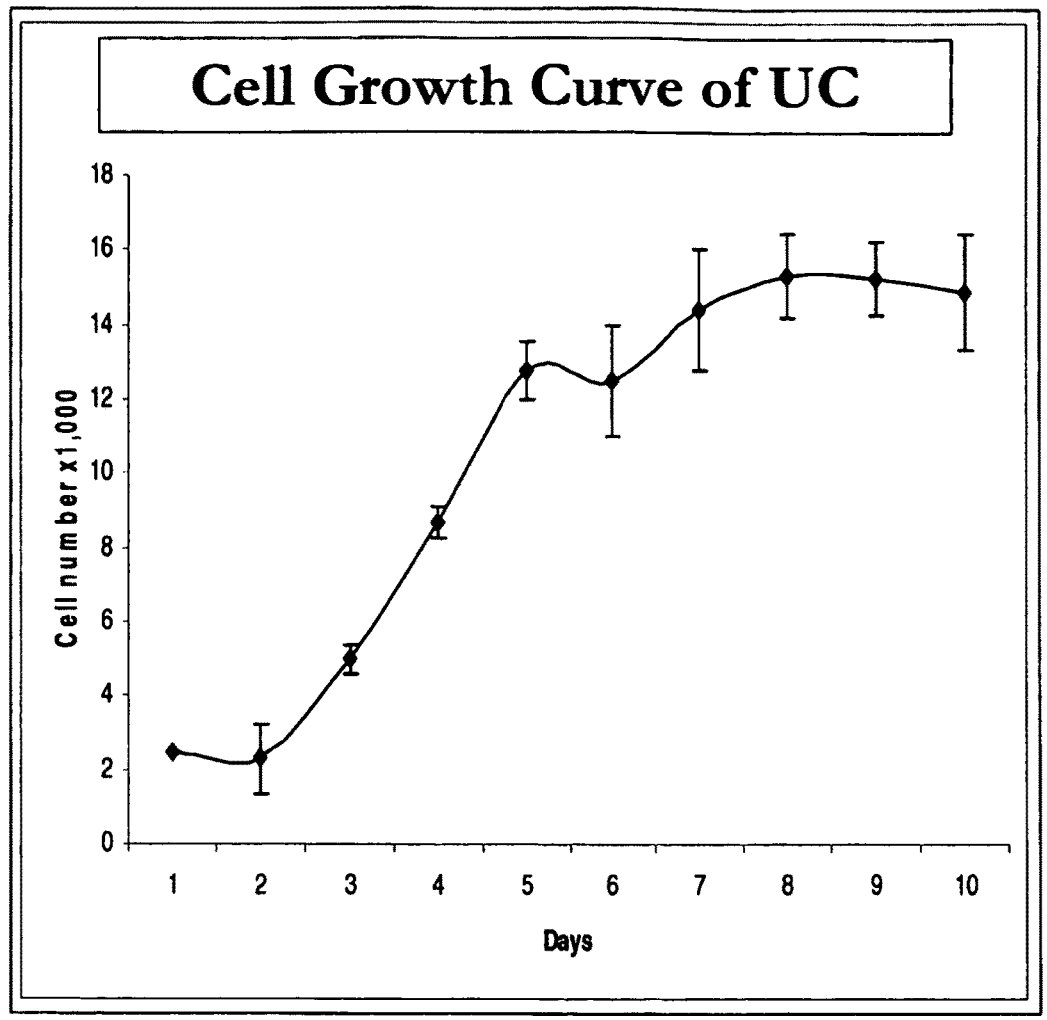
FIG. 3. Cell growth curve of urine cell cultures. Cells grew from a single cell to confluence in a 6-cm culture dish in 10 to 12 days.

It seems that there are mixed cell populations in urine: progenitor cells and mature cells as well. Urine was found to contain urothelial progenitor cells and smooth muscle progenitor cells. These cells were confirmed with CD markers as indicated above. In addition, urothelial progenitor cell markers and smooth muscle cell markers were employed to further characterize these cells. Monoclonal antibodies against urothelial progenitor cell-specific markers, uroplakin Ia and cytokeratins 7, 13, 17, and 19, were applied at 70% cell confluence, at the following dilutions for each antibody: anti-cytokeratin 7, 1:200; anti-cytokeratin 13, 1:100; anti-cytokeratin 17, 1:100; and anti-cytokeratin 19, 1:100. The expression of uroplakin and the indicated cytokeratins in urine progenitor cells was determined and compared with the expression of the markers in cultured urothelium obtained from regular biopsy tissue (Zhang, et al. (2003) *Adv. Exp. Med. Biol.* 539:907; Ludwikowski, et al. (1999) *BJU Int.* 84:507; Sugasi, et al. (2000) *J. Urol.* 164:951; Zhang, et al. (2001) *In Vitro Cell Dev. Biol. Anim.* 37:419) as well as normal human bladder mucosa (Southgate et al., *Lab Investigation* (1994) 71:583). The degree of immunofluorescence was defined as ranging from negative (−) to strongly positive (++++). Similar to cultured urothelium obtained from tissue biopsy, urine cells expressed uroplakin Ia and cytokeratins (CK) 7, 13, 17, and 19 (FIG. 3 and Table 3).

TABLE 3

| | Normal Human Bladder Mucosa | | | Cultured | |
|---|---|---|---|---|---|
| Specificity | Basal Cells | Intermediate Cells | Superficial Cells | Urothelium from Biopsy | Cultured Urine Cells |
| CK7 | ++ | ++ | ++ | +++ | ++ |
| CK13 | ++ | ++ | − | + | + |
| CK17 | ++ | ++/− | ++/− | ++ | ++ |
| CK19 | ++ | ++/− | ++ | ++ | ++ |
| Uroplakin Ia | − | − | +++ | ++ | ++ |

Figure 4:
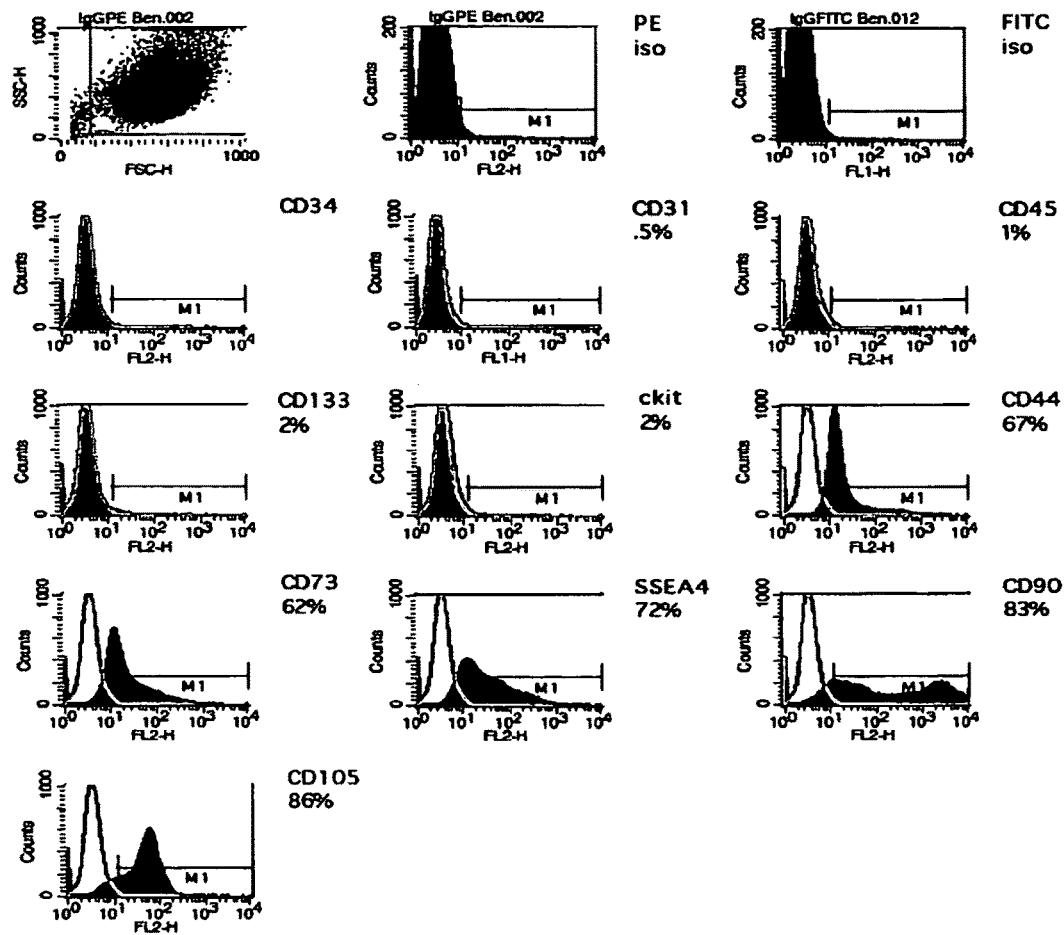
FIG. 4. Graphs of fluorescence activated cell sorting (FACS) demonstrate the presence of progenitor cell markers such as CD44, 105, 73, 90 and 133 in cells isolated from urine.

Moreover, compared to native bladder cells, cells obtained from urine expressed smooth muscle cell-specific markers, alpha smooth muscle actin (ASMA), desmin, myosin and calponin, as determined by immunofluorescence (FIG. 4 and Table 4).

TABLE 4

| | Normal Human Bladder Tissue | | | Cultured | |
|---|---|---|---|---|---|
| Specificity | SMC | Myo-fibroblast | Interstitial Cells | Urothelium from Biopsy | Cultured Urine Cells |
| ASMA | ++++ | +++ | +++ | ++++ | +++ |
| Desmin | ++ | − | − | + | + |
| Myosin | ++ | − | − | + | + |
| Calponin | +++ | − | − | +++ | +++ |
| C-Kit | | | | + | + |

Example 3

Cell Contractility and Tight Junctions of Urine Progenitor Cells

Functional characteristics of urine-derived smooth muscle cells are ascertained by determining cell contractility with collagen lattices. Methods for the collagen lattice contraction assay are known in the art (Kropp, et al. (1999) *J. Urol.* 162:1779). Contractile response to agonists is performed in a similar manner except that agonists are added to the serum-free media immediately prior to lattice release. Agonists which are tested include the Ca-ionophore A23187 (1025 M) and KCl.

Urine-derived urothelial progenitor cells are analyzed for tight junctions. Urothelial barrier function is maintained by apical membrane plaques and intercellular tight junctions. Tight junction components within urine progenitor cells is investigated with conventional methods such as electric microscopy (Zhang, et al. (2003) *Adv. Exp. Med. Biol.* 539:907; Ludwikowski, et al. (1999) *BJU Int.* 84:507; Sugasi, et al. (2000) *J. Urol.* 164:951; Zhang, et al. (2001) *In Vitro Cell Dev. Biol. Anim.* 37:419; Cross, et al. (2005) *Am. J. Physiol. Renal Physiol.* 289:F459).

Example 4

Urine Progenitor Cell Differentiation into Smooth Muscle Cells

To determine the effect of epithelial-stromal cell interaction or cell-cell interaction on urine progenitor cell differentiation into smooth muscle cells (Staack, et al. (2005)

*Differentiation* 73:121; DiSandro, et al. (1998) *J. Urol.* 160:1040), two co-culture methods are used. The first is an indirect co-culture using transwell devices with a 4.5 μm size exclusion. Urine smooth muscle progenitor cells are plated on the upper chamber wells and bladder smooth muscle cells and/or urothelium from tissue biopsy are seeded on the bottom wells of a transwell unit (Luk, et al. (2005) *J. Immunol. Methods* 305:39; Gerstenfeld, et al. (2003) *Connect Tissue Res.* 44 (suppl 1):85). The second method is a direct co-culture approach which is performed with a transwell insert of 0.4 μM pore size. The transwell is used as a basement membrane on which urine progenitor cells are cultured on the lower side, while normal human bladder urothelium and smooth muscle cells are cultured on the opposite upper side (Le Visage, et al. 92004) *Tissue Eng.* 10:1426). The urine cells are subsequently evaluated through phenotypic appearance, molecular analysis and immunohistochemical staining for smooth muscle protein expression on days 3, 7, 14, and 28 after cell seeding.

Example 5

Scaffolds Seeded with Urine Progenitor Cells

Cell attachment, proliferation and differentiation of urine progenitor cells on bladder submucosa membrane (BSM) and small intestine submucosa (SIS) was evaluated to determine the cell-matrix interaction for clinical application. In in vitro cell-seeded constructs, urine progenitor cell-derived urothelium was seeded on the BSM mucosal side and urine progenitor cell-derived smooth muscle cells on the serosa side placed in the presence of mixed media (KSFM:DMEM, 1:1).

Subsequently, the seeded matrices were implanted subcutaneously into athymic mice. The implanted engineered tissues were retrieved and assessed via histochemistry (H&E and Trichrom), immunohistochemistry (cytokeratin and smooth muscle cell-specific markers), western blot analyses, and human X/Y chromosome detection assay (FISH). For histochemical and immunohistochemical analysis, engineered tissues were fixed in 10% neutral-buffered formalin, dehydrated, and embedded in paraffin, using standard procedures. Five-mm sections were cut and mounted. Routine hematoxylin and eosin (H&E) staining and Masson's trichrome staining were performed. Immunohistochemical staining was also performed using monoclonal antibodies against smooth muscle cell proteins, alpha-smooth muscle actin (diluted 1:1000), desmin (1:20), calponin (1:50) and myosin (1:100) and against urothelial cell-specific protein, cytokeratin AE 1/AE3 (1:100 antibody dilution) (Zhang, et al. (2005) *BJU Int.* 96:1120; Zhang, et al. (2003) *Adv. Exp. Med. Biol.* 539:907; Zhang, et al. (2000) *J. Urol.* 164:928; Zhang, et al. (2006) *BJU Int.* 98:1100; Zhang, et al. (2004) *Tissue Eng.* 10:181; Zhang, et al. (2001) *In Vitro Cell Dev. Biol. Anim.* 37:419).

Proteins for western blot analysis were isolated by lysing cells or the cell-seeded scaffold tissue with a lysis buffer according to known methods (Zhang, et al. (2005) *BJU Int.* 96:1120; Lin, et al. (2004) *J. Urol.* 171:1348). Mouse anti-human alpha-smooth muscle actin, desmin, myosin, and AE1/AE3 were used as the primary antibody and peroxidase-labeled goat anti-mouse IgG as the secondary antibody. The presence of protein bands was detected by a commercially available enhanced chemiluminescence assay kit.

Figure 5:
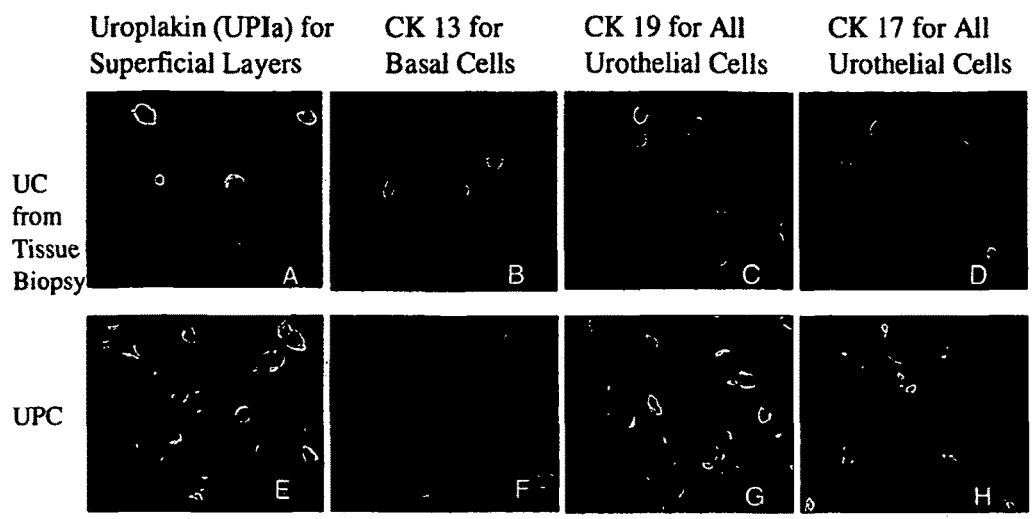
FIG. 5. Microscopy images of immunofluorescence staining with uroplakin (UPIa), cytokeratin 7, 13, 19, 17 and nucleic acid in human urothelium obtained from bladder biopsy (A-D) and UPCs (E-H).

Urine progenitor cells were noted in the graft tissues with LacZ staining one month after implantation. The implanted cells were also confirmed by human X/Y chromosome. Advantageously, urine progenitor cells formed multilayered urothelial cells and smooth muscle-like tissue structures within the scaffolds in vivo (FIG. 5). Furthermore, no tumor was observed in the graft tissues three months after implantation.

These data therefore provide in vitro and in vivo evidence that cells obtained from urine can serve as a source for bladder tissue engineering. Urine progenitor cells are readily available, and it has been shown that they proliferate and differentiate into urothelium and smooth muscle in vitro. Bladder cells derived from urine progenitor cells show urothelium and smooth muscle-like phenotypes including expressing urothelium and smooth muscle-specific proteins, respectively. Collagen matrix supports the three-dimensional growth of urine progenitor cells, which is a basic requirement for bladder reconstruction. In vivo urine progenitor cells-seeded scaffolds provide a cost-effective method for bladder reconstruction.

The foregoing is illustrative of the present invention, and is not to be construed as limiting thereof. The invention is defined by the following claims, with equivalents of the claimed to be included therein.

That which is claimed is:

1. A method for producing a culture of urine progenitor cells, said method comprising:
   providing a urine sample; and then
   isolating said urine progenitor cells from said urine sample, wherein said isolating step comprises:
   (a) collecting cells from said urine sample to provide a crude cell sample;
   (b) washing the crude cell sample to provide a washed cell sample; and
   (c) selecting said urine progenitor cells from said washed cell sample, wherein selecting urine progenitor cells comprises:
      (i) plating the washed cell sample in a medium that promotes the growth of urine progenitor cells;
      (ii) identifying said urine progenitor cells; and
      (iii) culturing said urine progenitor cells,
   wherein said urine progenitor cells are positive for CD117 (C-kit), SSEA-4, CD105, CD73, CD90, CD133 and CD44, and are negative for CD31, CD34 and/or CD45.

2. The method of claim 1, wherein identifying said urine progenitor cells comprises:
   (a) identifying said urine progenitor cells based upon morphology; or
   (b) identifying said urine progenitor cells based upon a marker specific to urine progenitor cells.

3. The method of claim 1, wherein said collecting step is carried out by centrifugation of said urine sample.

4. The method of claim 1, wherein said crude cell sample is washed in phosphate buffered saline.

5. The method of claim 2, wherein said identifying is carried out by selecting cells of interest based upon morphology.

6. The method of claim 2, wherein said identifying is carried out by selecting a marker specific to urine progenitor cells.

7. The method of claim 2, wherein said identifying is carried out by selecting a marker specific to urine progenitor cells, and wherein said selecting of said marker is carried out by FACS.

8. The method of claim 6, wherein said marker of said identifying is selected from the group consisting of: C-kit (CD117), SSEA-4, CD105, CD73, CD90, CD133, and CD44.

9. The method of claim 1, wherein said urine progenitor cells are from a mammalian subject.

10. The method of claim 1, further comprising the step of differentiating said urine progenitor cells into at least one of the group consisting of: urothelial cells and smooth muscle cells.

11. The method of claim 1, wherein said crude cell sample is washed in phosphate buffered saline comprising serum.

12. The method of claim 1, wherein said urine progenitor cells are from a human subject.

13. The method of claim 1, wherein said urine progenitor cells do not require feeder cells for growth or differentiation.

14. The method of claim 1, wherein said urine progenitor cells can differentiate into urothelium or smooth muscle.

15. The method of claim 5, wherein said identifying comprises identifying cells having a small, brighter-looking morphology compared to other cells in the sample when observed through a microscope as urine progenitor cells.

16. The method of claim 1, wherein said culturing comprises passaging said urine progenitor cells.

17. The method of claim 1, further comprising differentiating said urine progenitor cells into endothelial cells or interstitial cells.

18. The method of claim 6, wherein said marker of said identifying is selected from the group consisting of: C-kit (CD117), SSEA-4, CD73, and CD90.

* * * * *

UNITED STATES PATENT AND TRADEMARK OFFICE
CERTIFICATE OF CORRECTION

PATENT NO. : 10,398,804 B2
APPLICATION NO. : 12/601028
DATED : September 3, 2019
INVENTOR(S) : Zhang et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1241 days.

Signed and Sealed this
Second Day of June, 2020

Andrei Iancu
*Director of the United States Patent and Trademark Office*